(12) United States Patent
Niedermeier et al.

(10) Patent No.: US 7,300,964 B2
(45) Date of Patent: Nov. 27, 2007

(54) CARBON BLACK

(75) Inventors: Werner Niedermeier, Brühl (DE);
Joachim Fröhlich, Bornheim (DE);
Klaus Bergemann, Kerpen-Sindorf (DE); Egon Fanghänel, Halle (DE);
Bernd Knackfuss, Leipzig (DE);
Thomas Lüthge, Hanau (DE)

(73) Assignee: Degussa AG, Düsseldorf (DE)

( * ) Notice: Subject to any disclaimer, the term of this patent is extended or adjusted under 35 U.S.C. 154(b) by 526 days.

(21) Appl. No.: 10/911,948

(22) Filed: Aug. 4, 2004

(65) Prior Publication Data

US 2005/0031528 A1 Feb. 10, 2005

(30) Foreign Application Priority Data

Aug. 8, 2003 (DE) ............... 103 36 575

(51) Int. Cl.
*C08K 3/04* (2006.01)
*C01D 3/00* (2006.01)

(52) U.S. Cl. .................... 523/495; 423/449.1

(58) Field of Classification Search ........... 423/449.1, 423/449.2, 449.3; 524/495
See application file for complete search history.

(56) References Cited

U.S. PATENT DOCUMENTS 5,859,120 A 1/1999 Karl et al.
6,099,818 A 8/2000 Freund et al.
2001/0036994 A1* 11/2001 Bergemann et al. ......... 524/495
2002/0096089 A1* 7/2002 Bergemann et al. ......... 106/472

FOREIGN PATENT DOCUMENTS

| DE | 195 21 565 A1 | 1/1997 |
|---|---|---|
| DE | 196 13 796 A1 | 10/1997 |
| DE | 198 39 925 A1 | 10/1999 |
| DE | 100 12 784 A1 | 9/2001 |
| DE | 100 12 783 A1 | 10/2001 |
| EP | 0 569 503 | 8/1992 |
| EP | 0 949 303 A1 | 10/1999 |
| EP | 1293529 A2 * | 3/2003 |
| WO | WO 96/18690 | 6/1996 |
| WO | WO 98/42778 * | 10/1998 |
| WO | WO 98/45361 | 10/1998 |

* cited by examiner

*Primary Examiner*—Stuart L. Hendrickson
*Assistant Examiner*—Daniel C. McCracken
(74) *Attorney, Agent, or Firm*—Robert G. Weilacher; Smith, Gambrell & Russell

(57) ABSTRACT

Carbon black having organic groups, the organic group containing a thiocyanate group. Also described is a process for the production of the carbon black, wherein carbon black is reacted with organic compounds containing a C—C double or triple bond, which is not part of an aromatic system, whose C—C double or triple bond is activated by at least one substituent, and the organic compound contains at least one thiocyanate group. The carbon black according to the invention can be used in rubber compounds.

13 Claims, 3 Drawing Sheets

CARBON BLACK

INTRODUCTION AND BACKGROUND

The invention relates to a carbon black, a process for its production and its use.

Carbon blacks having organic groups are known from DE 10012783, wherein the organic group contains at least one substituted C—C single or double bond, is linked to the carbon black by means of the two carbon atoms in the C—C single or double bond and at least one carbon atom in the C—C single or double bond contains at least one activating substituent.

A process for the surface modification of carbon-containing material having aromatic groups by electrochemical reduction of a diazonium salt is known from EP 0569503.

The providing of carbon black with organic groups by linking the organic groups to the carbon-containing material by azo coupling (WO 96/18690) or by bonding the organic groups to the carbon black by means of reactions with radical formers (Ohkita K., Tsubokawa N., Saitoh E., Carbon 16 (1978) 41, DE 10012784.3) is also known.

A disadvantage of the known carbon blacks is that when surface-modified carbon blacks are used in rubber compounds, the hysteresis (correlated with rolling resistance) and/or the dynamic rigidity (correlated with handling properties) deteriorates.

SUMMARY OF THE INVENTION

The object of the present invention is to provide a carbon black that in a rubber compound has a higher or an equal dynamic rigidity (E* 60° C.) combined with reduced hysteresis (tan δ 60° C.).

The invention provides a carbon black having organic groups, which is characterized in that the organic group contains a thiocyanate group.

In a preferred embodiment the organic group can be a thiocyanate alkyl or thiocyanate aryl group, preferably an N-(4-thiocyanate alkyl)succinimide, N-(4-thiocyanate aryl)succinimide, N-(4-thiocyanate alkyl)amide or N-(4-thiocyanate aryl)amide group, particularly preferably an N-(4-thiocyanatophenyl) succinimide or N-(4-thiocyanatophenyl) amide group. The alkyl group can be a divalent branched or unbranched, saturated or unsaturated hydrocarbon having 1 to 20 C atoms. The aryl group can be a phenyl or naphthyl group.

The invention also provides a process for the production of the carbon black having organic groups according to the invention, which is characterized in that carbon black is reacted with organic compounds containing a C—C double or triple bond, which is not part of an aromatic system, whose C—C double or triple bond is activated by at least one substituent, and the organic compound contains at least one thiocyanate group.

Activating substituents can be acceptor substituents. Acceptor substituents can be —COOR, —CO—R, —CN, —SO$_2$R, —SO$_2$OR, —CO—X—CO— where R=H, —NH—R$^1$, alkyl, aryl or functionalized alkyl or aryl, X=O or N—R$^1$, R$^1$=alkyl, Y-functionalized alkyl, polymers, cyclic organic groups, aryl or Y-functionalized aryl in the form Ar—Y$_n$ (n=1-5), Y=—OH, —SH, —SO$_3$H, —SO$_3$M, —B(OH)$_2$, —O(CH$_2$—CH$_2$—O)$_n$H, —COOH, —NH$_2$, —NR$_2$, —N((CH$_2$—CH$_2$—O)$_n$H)$_2$, CON((CH$_2$—CH$_2$—O)$_n$ H)$_2$, trialkoxysilyl, perfluoroalkyl, R$^1$, —NH$_3^+$, —NR$_3^+$, —SO$_2$—NR$_2$, —NO$_2$, —Cl, —CO—NR$_2$, —SS— or —SCN, M=metal, for example alkali$^+$ or alkaline-earth$^{++}$, or NR$^2_4{}^+$ where R$^2$=H, alkyl or aryl.

In a preferred embodiment the organic compound can contain a thiocyanate alkyl or thiocyanate aryl group, preferably an N-(4-thiocyanate alkyl)succinimide, N-(4-thiocyanate aryl)succinimide, N-(4-thiocyanate alkyl)amide or N-(4-thiocyanate aryl)amide group, particularly preferably an N-(4-thiocyanatophenyl)succinimide or N-(4-thiocyanatophenyl)amide group.

The carbon blacks having organic groups according to the invention can be produced by reacting the starting carbon blacks with N-(4-thiocyanatophenyl) maleic acid imide or N-(4-thiocyanatophenyl) maleic acid amide. One possible reaction mechanism could be:

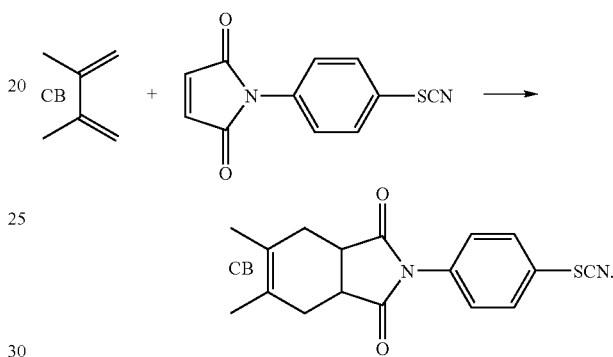

N-(4-thiocyanatophenyl) maleic acid imide and N-(4-thiocyanatophenyl) maleic acid amide can be produced from maleic anhydride and thiocyanatoaniline. The symbol "CB" stands for carbon black.

Furnace black, gas black, channel black, lamp black, thermal black, acetylene black, plasma black, inversion blacks, known from DE 195 21 565 and DE 19839925, Si-containing carbon blacks, known from WO 98/45361 or DE 19613796, or metal-containing carbon blacks, known from WO 98/42778, arc black and carbon blacks that are secondary products of chemical production processes can be used as starting carbon blacks. The carbon black can be activated by preliminary reactions, by oxidation for example. Carbon black for pigment application can be used. Other carbon blacks can be: conductive carbon black, carbon black for UV stabilization, carbon black as a filler in systems other than rubber, for example in bitumen, plastics, carbon black as a reducing agent, in metallurgy.

Another process for the production of the carbon black having organic groups according to the invention is characterized in that carbon black is reacted with a diazonium salt and the diazonium salt contains a thiocyanate group.

The diazonium salt can be produced by reacting a primary amine with sodium nitrite, preferably in acid solution. 4-Thiocyanatoaniline, for example, can be used as the primary amine.

The invention also provides a rubber compound that is characterized in that it contains a rubber or a blend of rubbers and the carbon black having organic compounds according to the invention.

Natural rubber and/or synthetic rubbers can be used as the rubber. Preferred synthetic rubbers are described for example in W. Hofmann, Kautschuktechnologie, Genter Verlag, Stuttgart 1980. They can include, inter alia, polybutadiene (BR)

polyisoprene (IR)

styrene/butadiene copolymers having styrene contents of 1 to 60, preferably 5 to 50 wt. % (SBR)

isobutylene/isoprene copolymers (IIR)

butadiene/acrylonitrile copolymers having acrylonitrile contents of 5 to 60, preferably 10 to 50 wt. % (NBR)

ethylene/propylene/diene copolymers (EPDM) and blends of these rubbers.

In a preferred embodiment the rubbers can be capable of vulcanization with sulfur.

The rubber compounds can contain 10 to 150 parts by weight of carbon black having organic groups, the parts by weight relating to 100 parts by weight of rubber.

The rubber compounds can contain organosilanes in a quantity of 0.1 to 15 wt. %, relative to the quantity of filler used. Alkyl silanes, for example octyl trimethoxysilane, hexadecyl trimethoxysilane, octadecyl trimethoxysilane, propyl triethoxysilane or octyl triethoxysilane, or organopolysulfane silanes, for example bis-(triethoxysilylpropyl)tetrasulfane or bis-(triethoxysilylpropyl)disulfane, can be used as organosilanes.

The rubber compounds according to the invention can contain other known rubber auxiliary substances, such as e.g. crosslinking agents, vulcanization accelerators, reaction accelerators, reaction retarders, antioxidants, stabilizers, processing aids, plasticizers, waxes, metal oxides and activators, such as triethanolamine, polyethylene glycol or hexanetriol.

The rubber auxiliary substances can be used in conventional quantities, which are governed inter alia by the intended application. Conventional quantities are for example quantities of 0.1 to 50 wt. %, relative to rubber.

Sulfur or organic sulfur donors can be used as crosslinking agents.

The rubber compounds according to the invention can also contain vulcanization accelerators. Examples of suitable vulcanization accelerators are mercaptobenzothiazoles, sulfenamides, guanidines, thiurams, dithiocarbamates, thioureas and thiocarbonates. The vulcanization accelerators and sulfur can be used in quantities of 0.1 to 10 wt. %, preferably 0.1 to 5 wt. %, relative to the rubber used.

The invention also provides a process for the production of the rubber compounds according to the invention, which is characterized in that the rubber or the blend of rubbers and the carbon black having organic groups according to the invention are mixed in a mixer.

Mixing of the rubbers with the carbon black having organic groups according to the invention, optionally rubber auxiliary substances and organosilanes can be performed in conventional mixers, such as rolls, internal mixers and compounding extruders. Such rubber compounds can conventionally be produced in internal mixers, the rubbers, the filler and the rubber auxiliary substances being first mixed together in one or more successive thermomechanical mixing stages at 100 to 170° C. The sequence and time of addition of the individual components can have a decisive influence on the properties of the compound obtained. The crosslinking chemicals can conventionally be added to the rubber compound thus obtained in an internal mixer or on a roll at 40-110° C. and the compound processed into the so-called raw compound for the subsequent processing steps, such as moulding and vulcanization, for example.

Vulcanization of the rubber compounds according to the invention can take place at temperatures of 80 to 200° C., preferably 130 to 180° C., optionally under a pressure of 10 to 200 bar.

The rubber compounds according to the invention can be used for the production of moulded articles, for example for the production of pneumatic tires, tire treads, cable sheaths, tubes, drive belts, conveyor belts, roll coverings, tires, shoe soles, sealing rings, profiles and damping elements.

The invention also provides moulded articles obtainable from the rubber compound according to the invention by vulcanization.

The rubber compounds according to the invention have the advantage that the dynamic rigidity is the same or higher (equal or better handling properties) and at the same time the loss factor at 60° C. (hysteresis) is reduced (lower rolling resistance) in comparison to a rubber compound containing the unmodified starting carbon black.

BRIEF DESCRIPTION OF DRAWINGS

The present invention will be further understood with reference to the accompanying drawings, wherein.

DETAILED EMBODIMENTS OF THE INVENTION

EXAMPLE 1

Figure 1:
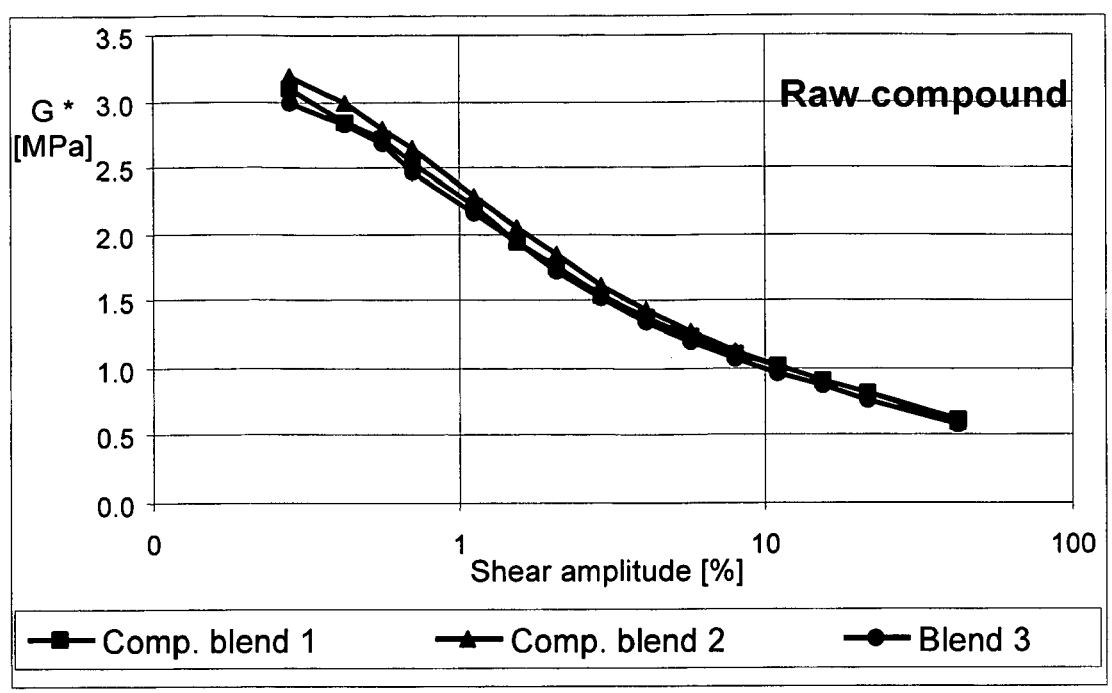
FIG. 1 is a graph showing RPA (rubber process analyzer) data of dynamic shear modulus as a function of shear amplitude for the raw unvulcanized rubber.
Figure 2:
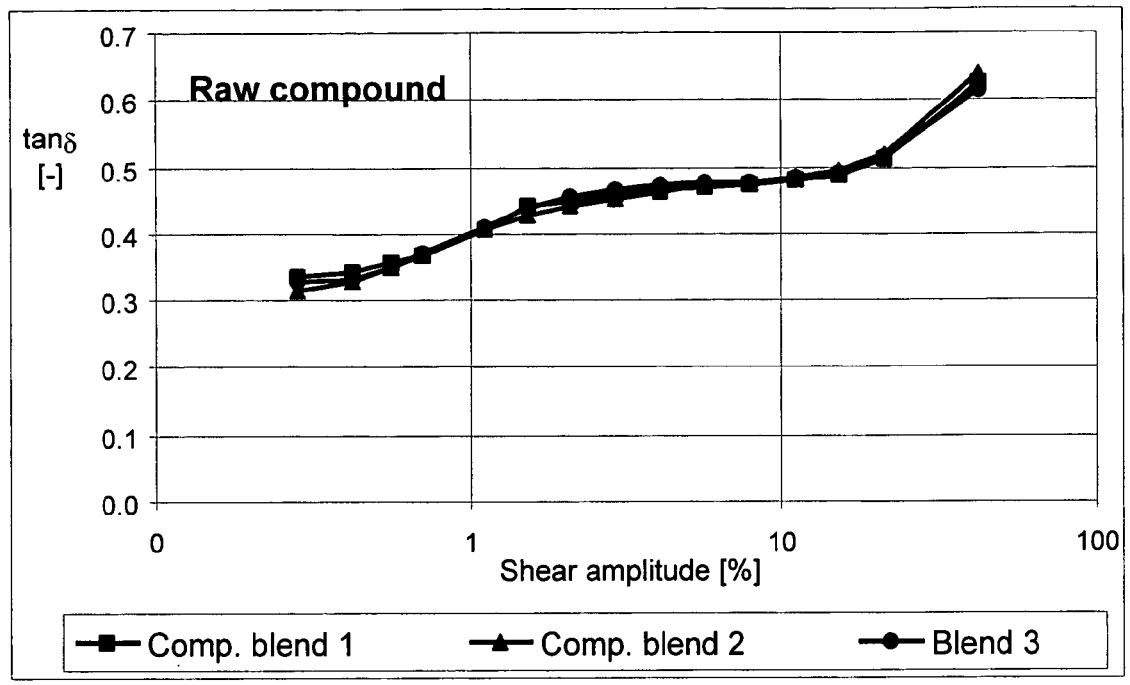
FIG. 2 is a graph showing RPA data of hysteresis as a function of shear amplitude for the raw unvulcanized rubber.

Production of the carbon black having organic groups according to the invention by reacting N-(4-thiocyanatophenyl) maleic acid amide with carbon black in a dry mix.

500 g of carbon black N 220 and 100 g of N-(4-thiocyanatophenyl) maleic acid amide are mixed for 5 minutes in a mixer and then tempered for 5 hours in a muffle furnace at 180° C. On completion of tempering the carbon black, in ten portions, is suspended in 1 liter of acetone per portion, extracted, washed with acetone and dried.

After the reaction the product is pulverized by grinding.

Conversion: 70% (relative to the N-(4-thiocyanatophenyl) maleic acid amide used)

EXAMPLE 2

Production of the carbon black having organic groups according to the invention by reacting N-(4-thiocyanatophenyl) maleic acid amide with carbon black in solution.

500 g of carbon black N 220 are suspended in a solution of 34 g of maleic acid amide of 4-thiocyanatoaniline in 10 liters of acetone. The solvent is then removed by distillation. The remaining carbon black-reagent blend is tempered for 5 hours in a muffle furnace at 180° C. On completion of tempering the carbon black, in ten portions, is suspended in 1 liter of acetone per portion, extracted, washed with acetone and dried.

After the reaction the product is pulverized by grinding.

Conversion: 82% (relative to the N-(4-thiocyanatophenyl) maleic acid amide used.

EXAMPLE 3

Production of the carbon black having organic groups according to the invention by reacting N-(4-thiocyanatophenyl) maleic acid amide with carbon black in solution.

500 g of carbon black N 220 are suspended in a solution of 67 g of maleic acid amide of 4-thiocyanatoaniline in 10 liters of acetone. The solvent is then removed by distillation. The remaining carbon black-reagent blend is tempered for 5 hours in a muffle furnace at 180° C. On completion of tempering the carbon black, in ten portions, is suspended in 1 liter of acetone per portion, extracted, washed with acetone and dried.

After the reaction the product is pulverized by grinding.

Conversion: 87% (relative to the N-(4-thiocyanatophenyl) maleic acid amide used).

EXAMPLE 4

Production of the carbon black having organic groups according to the invention by reacting N-(4-thiocyanatophenyl) maleic acid amide with carbon black in solution.

500 g of carbon black N 220 are suspended in a solution of 100 g of maleic acid amide of 4-thiocyanatoaniline in 10 liters of acetone. The solvent is then removed by distillation. The remaining carbon black-reagent blend is tempered for 5 hours in a muffle furnace at 180° C. On completion of tempering the carbon black, in ten portions, is suspended in 1 liter of acetone per portion, extracted, washed with acetone and dried.

After the reaction the product is pulverised by grinding.

Conversion: 70% (relative to the N-(4-thiocyanatophenyl) maleic acid amide used)

COMPARATIVE EXAMPLE 1

Production of OH-surface-modified carbon black in solution according to DE 10012783.

500 g of carbon black N 220 are suspended in a solution of 100 g of maleic acid amide of 4-hydroxyaniline in 10 liters of acetone. The solvent is then removed by distillation. The remaining carbon black-reagent blend is tempered for 5 hours in a muffle furnace at 180° C. On completion of tempering the carbon black, in ten portions, is suspended in 1 liter of acetone per portion, extracted, washed with acetone and dried.

After the reaction the product is pulverized by grinding.

Conversion: 70%

COMPARATIVE EXAMPLE 2

Production of surface-modified carbon black by reacting N-(4-sulfamoylphenyl) maleic acid amide with carbon black according to DE 10012783 in a dry mix.

500 g of N 220 and 70 g of N-(4-sulfamoylphenyl) maleic acid amide are mixed in a mixer for 5 minutes and then tempered for 5 hours at 180° C. After the reaction the product is pulverised by grinding.

Conversion: (relative to the N-(4-sulfamoylphenyl) maleic acid amide used) 59%

EXAMPLE 5

Rubber Compounds

The formulation used for the rubber compounds is shown in Table 1. The unit phr denotes parts by weight relative to 100 parts of the crude rubber used. The general process for the production of rubber compounds and vulcanizates thereof is described in the following book: "Rubber Technology Handbook", W. Hofmann, Hanser Verlag 1994.

TABLE 1

| Substance | Comp. blend 1 [phr] | Comp. blend 2 [phr] | Blend 3 [phr] |
|---|---|---|---|
| Step 1 | | | |
| Buna SBR 1500 | 100 | 100 | 100 |
| Carbon black N 220 | 60 | — | — |
| Comparative example 1 | — | 60 | — |
| Carbon black having organic groups according to the invention according to example 1 | — | — | 60 |
| ZnO RS | 3 | 3 | 3 |
| Edenor ST1 GS | 2 | 2 | 2 |
| Protektor G3108 | 1 | 1 | 1 |
| Step 2 | | | |
| Batch from step 1 | | | |
| Step 3 | | | |
| Batch from step 2 | | | |
| Vulkacit CZ | 1.5 | 1.5 | 1.5 |
| Sulfur | 1.5 | 1.5 | 1.5 |

The polymer Buna SBR 1500 is an emulsion-polymerized SBR copolymer from Buna SOW Leuna Olefinverbund GmbH having a styrene content of 23.5% and a viscosity ML(1+4) 100° C. of 50.

Edenor ST1 GS from Caldic Deutschland GmbH is used as stearic acid and Protektor G3108 is a wax produced by Paramelt B.V. Vulkacit CZ (CBS) is a commercial product from Bayer AG.

Carbon black N 220 is an ASTM carbon black and is produced by Degussa AG as Corax N 220.

The rubber compounds are produced in an internal mixer according to the mixing instructions in Table 2.

TABLE 2

| Step 1 | |
|---|---|
| Settings | |
| Mixer | Rheomix 600 P |
| Speed | 100 min$^{-1}$ |
| Ram force | 5.5 bar |
| Empty volume | 0.08 l |
| Fill ratio | 0.7 |
| Flow temp. | 90° C. |
| Mixing process | |
| 0 to 1 min | Buna SBR 1500 |
| 1 to 2 min | ½ carbon black, stearic acid, ZnO |
| 2 to 3 min | ½ carbon black, Protector G3108 |
| 3 min | Vent |
| 3 to 4 min | Mix and remove |
| Batch temp. | 140-155° C. |
| Storage | 24 h at room temperature |

TABLE 2-continued

Step 2

Settings

| | |
|---|---|
| Mixer | As for step 1 apart from: |
| Flow temp. | 100° C. |
| Fill ratio | 0.68 |

Mixing process

| | |
|---|---|
| 0 to 2 min | Break up batch from step 1 |
| 2 min | Remove |
| Batch temp. | 140-155° C. |
| Storage | 4 h at room temperature |

Step 3

Settings

| | |
|---|---|
| Mixer | As for step 1 apart from |
| Speed | 50 min$^{-1}$ |
| Fill ratio | 0.66 |
| Flow temp. | 70° C. |

Mixing process

| | |
|---|---|
| 0 to 2 min | Batch from step 2, accelerator, sulfur |
| 2 min | Remove and sheet out on laboratory mixing rolls |
| | Homogenize: |
| | Score 3x on left, 3x on right and |
| | pass through 8x with narrow nip (1 mm) |
| | and 3x with wide nip (3.5 mm) |
| | Remove sheet. |
| Batch temp. | <110° C. |

The rubber test methods are summarised in Table 3.

TABLE 3

| Physical test | Standard/conditions |
|---|---|
| Cure-meter test, 165° C. | DIN 53529/3, ISO 6502 |
| Dmax – Dmin [dNm] | |
| Specimen 1, 23° C. | DIN 53504, ISO 37 |
| Tensile strength [MPa] | |
| Moduli [MPa] | |
| Elongation at break [%] | |
| Viscoelastic properties, MTS, | DIN 53 513, ISO 2856 |
| 60° C., 16 Hz, | |
| 50 N initial force and 25 N | |
| amplitude force | |
| Complex modulus E* [MPa] | |
| Loss factor tan δ [ ] | |

The results of the rubber test are summarized in Table 4.

TABLE 4

| Results Feature | Unit | Comparative blend 1 | Comparative blend 2 | Blend 3 |
|---|---|---|---|---|
| Vulcanization time | [min] | 30 | 30 | 30 |
| Dmin | [dNm] | 3.4 | 4.3 | 4.3 |
| Dmax – Dmin | [dNm] | 23.3 | 23.0 | 26.9 |
| Specimen 1 | | | | |
| Tensile strength | [MPa] | 23.5 | 23.5 | 22.2 |
| Modulus 50% | [Mpa] | 2.3 | 2.1 | 2.8 |
| Modulus 100% | [MPa] | 4.1 | 3.6 | 5.2 |
| Modulus 200% | [Mpa] | 11.9 | 8.6 | 13.0 |
| Modulus 300% | [MPa] | 22.0 | 15.1 | 21.5 |
| Elongation at break | [%] | 325 | 450 | 440 |
| MTS | | | | |
| E*, 60° C. | [MPa] | 16.5 | 16.4 | 18.7 |
| Loss factor tanδ 60° C. | [—] | 0.233 | 0.218 | 0.207 |

The rubber compound according to the invention displays a markedly higher Dmax-Dmin value in comparison to the reference blends. While the rubber compound according to the invention has a comparable modulus level at 300% elongation, the modulus at 100% elongation is markedly higher in comparison to the reference blends. This then also explains the higher dynamic rigidity E*. The tan δ 60° C. value is reduced in the rubber compound according to the invention (improved rolling resistance).

Figure 3:
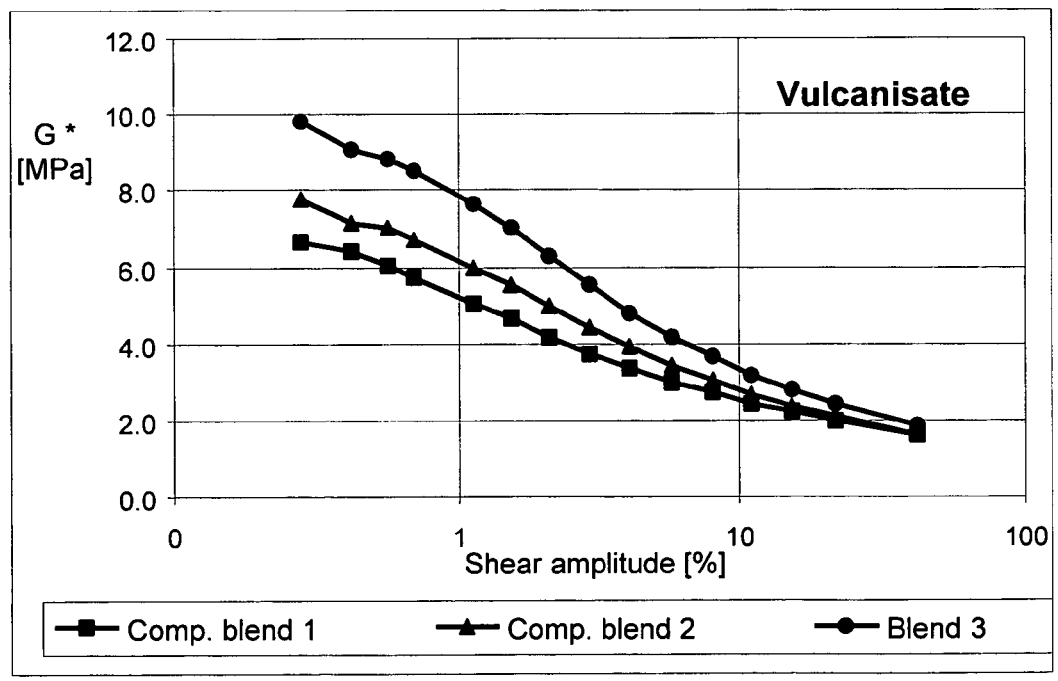
FIG. 3 is a graph showing RPA data of dynamic shear modulus as a function of shear amplitude for the vulcanized rubber of the invention.
Figure 4:
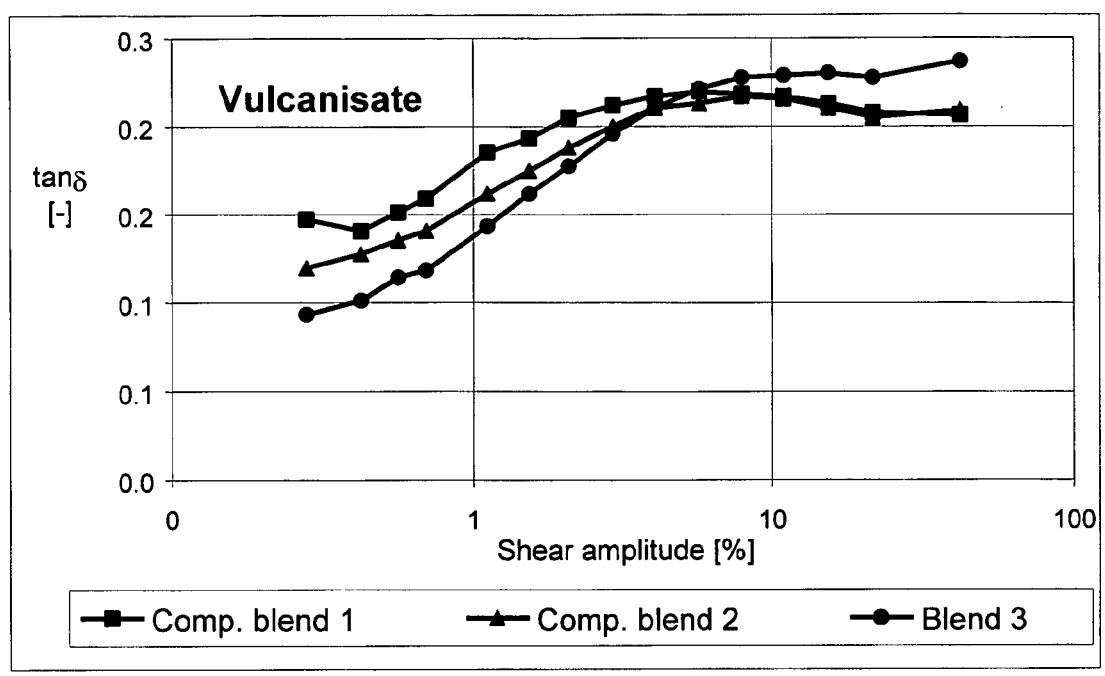
FIG. 4 is a graph showing RPA data of hysteresis as a function of shear amplitude for the vulcanized rubber of the invention.

The effect becomes even clearer in RPA measurement (FIGS. 1 to 4). While the comparative blends and the blend according to the invention display identical behaviour in the raw compound (Table 5), in terms of both G*(FIG. 1) and tan δ (FIG. 2), the behaviour changes after vulcanization (FIGS. 3+4/Table 6). In the vulcanizate the rubber compounds according to the invention are characterized in that they have a higher Payne effect and a lower tan δ value with small deflections.

TABLE 5

| Raw compound | Comparative blend 1 | Comparative blend 2 | Blend 3 |
|---|---|---|---|
| $G^*_{RC}@0.28\%$ | 3.1064 | 3.2006 | 2.9951 |
| $G^*_{RC}@42\%$ | 0.61969 | 0.59456 | 0.58877 |
| Delta_$G^*_{RC}$ | 2.48671 | 2.60604 | 2.40633 |
| $\tan\delta_{RC}@0.28\%$ | 0.335 | 0.315 | 0.328 |

TABLE 6

| Vulcanizate | Comparative blend 1 | Comparative blend 2 | Blend 3 |
|---|---|---|---|
| $G^*_V@0.28\%$ | 6.662 | 7.757 | 9.799 |
| $G^*_V@42\%$ | 1.628 | 1.619 | 1.867 |
| Delta_$G^*_V$ | 5.034 | 6.138 | 7.932 |
| $\tan\delta_V@0.28\%$ | 0.147 | 0.12 | 0.094 |

Description of the RPA Test Method:

The RPA data is measured with a rubber process analyzer (RPA) supplied by alpha-technologies (deformation type: shear torsion, temperature: 60° C., frequency: 1.6 Hz, dynamic shear amplitude: 0.28%-42%, 15 measuring points in ascending order distributed equidistantly along the logarithmic scale of shear amplitude). Plotting the dynamic shear modulus as a function of amplitude in the above amplitude range describes the Payne effect.

The measuring principle is described in J. Fröhlich and H. D. Luginsland, Rubber World, Vol. 224, No. 1, p. 28ff.

Procedure:

The amplitude sweep defined above is applied to a raw compound sample from the last productive step in each case in the RPA at 60° C. The dynamic modulus $G^*_{RC}$ and the loss factor tan $\delta_{RC}$ as a function of the shear amplitude are obtained as the measurement results. The actual Payne effect can be calculated as delta $G^*_{RC}:=G^*_{RC}@0.28\%-G^*_{RC}@42\%$. $G^*_{RC}$ and tan $\delta_{RC}$ at various amplitudes between 0.28% and 42% and delta_$G^*_{RC}$ represent the RPA data for the raw compound.

In an additional measurement, a new raw compound sample from the last productive step in each case is first vulcanised in the RPA at a vulcanization temperature T_vulc for a vulcanization time of t_vulc. Immediately thereafter, the sample vulcanized in this way is cooled in the RPA without opening the measuring chamber with the aid of compressed air (room temperature) until the measuring temperature of 60° C. has been reached and stabilized. Depending on the vulcanization temperature and the sample used, this process takes a few minutes—typically around 2 to 5 minutes—and is performed automatically by the RPA. Immediately thereafter, without opening the measuring chamber in the meantime, an amplitude sweep as defined above is applied to this vulcanized sample in the RPA at 60° C. The dynamic modulus $G^*_v$ and the loss factor tan $\delta_v$ as a function of the shear amplitude are obtained as the measuring results. The actual Payne effect can then be calculated as delta $G^*_v := G^*_v @0.28\% - G^*_v @42\%$. $G^*_v$ and tan $\delta_v$ at various amplitudes between 0.28% and 42% and delta_$G^*_v$ then represent the RPA data for the vulcanizate.

EXAMPLE 6

Rubber Compounds

The formulation used for the rubber compounds is shown in Table 7.

TABLE 7

| Substance | Comp. blend 4 [phr] | Blend 5 [phr] | Blend 6 [phr] | Blend 7 [phr] |
|---|---|---|---|---|
| Step 1 | | | | |
| Buna SBR 1500 | 100 | 100 | 100 | 100 |
| Carbon black N 220 | 60 | — | — | — |
| Carbon black | — | 60 | — | — |
| according to the invention according to example 2 | | | | |
| Carbon black | — | — | 60 | — |
| according to the invention according to example 3 | | | | |
| Carbon black | — | — | — | 60 |
| according to the invention according to example 4 | | | | |
| ZnO RS | 3 | 3 | 3 | 3 |
| Edenor ST1 GS | 2 | 2 | 2 | 2 |
| Protektor G3108 | 1 | 1 | 1 | 1 |
| Step 2 | | | | |
| Batch from step 1 | | | | |
| Step 3 | | | | |
| Batch from step 2 | | | | |
| Vulkacit CZ | 1.5 | 1.5 | 1.5 | 1.5 |
| Sulfur | 1.5 | 1.5 | 1.5 | 1.5 |

The rubber compounds are produced in an internal mixer according to the mixing instructions in Table 8.

TABLE 8

| Step 1 | |
|---|---|
| Settings | |
| Mixer | Brabender 350 S |
| Speed | 50 min$^{-1}$ |
| Ram force | 5.5 bar |
| Empty volume | 0.39 l |
| Fill ratio | 0.68 |
| Flow temp. | 90° C. |

TABLE 8-continued

| Mixing process | |
|---|---|
| 0 to 1 min | Buna SBR 1500 |
| 1 to 2 min | ½ carbon black, stearic acid, ZnO |
| 2 to 3 min | ½ carbon black, Protector G3108 |
| 3 min | Vent |
| 3 to 4 min | Mix and remove |
| Batch temp. | 145-155° C. |
| Storage | 24 h at room temperature |
| Step 2 | |
| Settings | |
| Mixer | As for step 1 apart from: |
| Flow temp. | 100° C. |
| Speed | 70 min$^{-1}$ |
| Fill ratio | 0.66 |
| Mixing process | |
| 0 to 2 min | Break up batch from step 1 |
| 2 min | Remove |
| Batch temp. | 145-155° C. |
| Storage | 24 h at room temperature |
| Step 3 | |
| Settings | |
| Mixer | Troster roll WNU1 |
| Speed front | 20 min$^{-1}$ |
| Speed rear | 24 min$^{-1}$ |
| Roll temp. front | 40° C. |
| Roll temp. rear | 50° C. |
| Mixing process | |
| 0 to 2 min | Batch from step 2, sheet out |
| 2 to 4 min | Incorporate accelerator, sulfur |
| 4 to 6 min | Score 3x on left, 3x on right and pass through 8x with narrow nip and 3x with wide nip Remove sheet. |
| Batch temp. | <110° C. |

The results of the rubber test are summarized in Table 9.

TABLE 9

| Results Feature | Unit | Comparative blend 4 | Blend 5 | Blend 6 | Blend 7 |
|---|---|---|---|---|---|
| Vulcanization time | [min] | 25 | 25 | 25 | 25 |
| Dmin | [dNm] | 3.2 | 3.2 | 3.2 | 3.3 |
| Dmax – Dmin | [dNm] | 23.0 | 24.8 | 25.3 | 25.6 |
| Specimen 1 | | | | | |
| Tensile strength | [MPa] | 17.5 | 26.0 | 22.5 | 22.1 |
| Modulus 50% | [Mpa] | 2.2 | 2.6 | 2.6 | 2.5 |
| Modulus 100% | [MPa] | 3.9 | 5.0 | 4.8 | 4.6 |
| Modulus 200% | [Mpa] | 11.9 | 14.4 | 13.4 | 11.8 |
| Modulus 300% | [MPa] | — | 24.6 | — | 20.5 |
| Elongation at break MTS | [%] | 260 | 315 | 290 | 320 |
| E*, 60° C. | [MPa] | 16.6 | 18.8 | 18.3 | 17.2 |
| Loss factor tan δ 60° C. | [—] | 0.193 | 0.175 | 0.155 | 0.151 |

The rubber compounds according to the invention display a markedly higher Dmax-Dmin value, modulus at low elongations and dynamic modulus (E* 60° C.) in comparison to the reference blend. The tan δ 60° C. is reduced (lower rolling resistance) in comparison to the reference blend.

EXAMPLE 7

Rubber Compounds

The formulation used for the rubber compounds is shown in Table 10.

TABLE 10

| Substance | Comp. blend 8 [phr] | Blend 9 [phr] | Blend 10 [phr] | Blend 11 [phr] |
|---|---|---|---|---|
| Step 1 | | | | |
| Buna VSL 5025-1 | 96 | 96 | 96 | 96 |
| Buna CB 24 | 30 | 30 | 30 | 30 |
| Carbon black N 220 | 80 | — | — | — |
| Carbon black according to the invention according to example 2 | — | 80 | — | — |
| Carbon black according to the invention according to example 3 | — | — | 80 | — |
| Carbon black according to the invention according to example 4 | — | — | — | 80 |
| ZnO RS | 3 | 3 | 3 | 3 |
| Edenor ST1 GS | 2 | 2 | 2 | 2 |
| Naftolen ZD | 10 | 10 | 10 | 10 |
| Vulkanox 4020 | 1.5 | 1.5 | 1.5 | 1.5 |
| Protektor G3108 | 1 | 1 | 1 | 1 |
| Step 2 | | | | |
| Batch from step 1 | | | | |
| Step 3 | | | | |
| Batch from step 2 | | | | |
| Vulkacit CZ | 1.5 | 1.5 | 1.5 | 1.5 |
| Sulfur | 1.5 | 1.5 | 1.5 | 1.5 |

The polymer VSL 5025-1 is a solution-polymerized SBR copolymer from Bayer AG with a styrene content of 25 wt. % and a butadiene content of 75 wt. %. The copolymer contains 37.5 phr oil and has a Mooney viscosity (ML 1+4/100° C.) of 50±4.

The polymer Buna CB 24 is a cis-1,4-polybutadiene (neodymium type) from Bayer AG with a cis-1,4 content of 97%, a trans-1,4 content of 2% and a 1,2-content of 1%.

Naftolen ZD from Chemetall is used as aromatic oil; Vulkanox 4020 is a 6PPD from Bayer AG.

The rubber compounds are produced in an internal mixer according to the mixing instructions in Table 11.

TABLE 11

| Step 1 | |
|---|---|
| Settings | |
| Mixer | Brabender 350 S |
| Speed | 80 min$^{-1}$ |
| Ram force | 5.5 bar |
| Empty volume | 0.39 l |
| Fill ratio | 0.68 |
| Flow temp. | 90° C. |
| Mixing process | |
| 0 to 1 min | Buna VSL 5025-1, Buna CB 24 |
| 1 to 3 min | ½ carbon black, stearic acid, ZnO, Naftolen ZD |

TABLE 11-continued

| 3 to 4 min | ½ carbon black, Vulkanox 4020, Protector G3108 |
|---|---|
| 4 min | Clean |
| 4 to 5 min | Mix and remove |
| Batch temp. | 145-155° C. |
| Storage | 24 h at room temperature |
| Step 2 | |
| Settings | |
| Mixer | As for step 1 apart from: |
| Speed | 95 min$^{-1}$ |
| Fill ratio | 0.66 |
| Mixing process | |
| 0 to 2 min | Break up batch from step 1 |
| 2 min | Remove |
| Batch temp. | 145-155° C. |
| Storage | 24 h at room temperature |
| Step 3 | |
| Settings | |
| Mixer | Troster roll WNU1 |
| Speed front | 20 min$^{-1}$ |
| Speed rear | 24 min$^{-1}$ |
| Roll temp. front | 40° C. |
| Roll temp. rear | 50° C. |
| Mixing process | |
| 0 to 2 min | Batch from step 2, sheet out |
| 2 to 4 min | Incorporate accelerator, sulfur |
| 4 to 6 min | Score 3x on left, 3x on right and pass through 8x with narrow nip and 3x with wide nip Remove sheet. |
| Batch temp. | <110° C. |

The results of the rubber test are summarized in Table 12.

TABLE 12

| Results Feature | Unit | Comparative blend 8 | Blend 9 | Blend 10 | Blend 11 |
|---|---|---|---|---|---|
| Vulcanization time | [min] | 35 | 35 | 35 | 35 |
| Dmin | [dNm] | 2.5 | 3.0 | 3.1 | 2.8 |
| Dmax – Dmin | [dNm] | 13.6 | 18.7 | 19.7 | 15.9 |
| Specimen 1 | | | | | |
| Tensile strength | [MPa] | 14.8 | 15.2 | 16.6 | 14.9 |
| Modulus 50% | [Mpa] | 1.5 | 1.5 | 1.6 | 1.5 |
| Modulus 100% | [MPa] | 2.8 | 2.8 | 3.0 | 2.7 |
| Modulus 200% | [Mpa] | 7.2 | 7.3 | 7.9 | 6.7 |
| Modulus 300% | [MPa] | 12.7 | 13.1 | 13.9 | 12.2 |
| Elongation at break | [%] | 340 | 335 | 350 | 355 |
| MTS | | | | | |
| E*, 60° C. | [MPa] | 10.8 | 16.7 | 17.6 | 14.7 |
| Loss factor tan δ 60° C. | [—] | 0.246 | 0.223 | 0.206 | 0.190 |

The rubber compounds according to the invention display a markedly higher Dmax-Dmin value, dynamic modulus (E* 60° C.) and a higher or equal modulus at low elongations in comparison to the reference blend. The tan δ 60° C. is reduced (lower rolling resistance) in comparison to the reference blend.

EXAMPLE 8

Rubber Compounds

The formulation used for the rubber compounds is shown in Table 13.

TABLE 13

| Substance | Comp. blend 12 [phr] | Blend 13 [phr] | Blend 14 [phr] | Blend 15 [phr] |
|---|---|---|---|---|
| Step 1 | | | | |
| Natural rubber | 100 | 100 | 100 | 100 |
| Carbon black N 220 | 52 | — | — | — |
| Carbon black according to the invention according to example 2 | — | 52 | — | — |
| Carbon black according to the invention according to example 3 | — | — | 52 | — |
| Carbon black according to the invention according to example 4 | — | — | — | 52 |
| ZnO RS | 3 | 3 | 3 | 3 |
| Edenor ST1 GS | 3 | 3 | 3 | 3 |
| Vulkanox HS/LG | 1 | 1 | 1 | 1 |
| Vulkanox 4020 | 1 | 1 | 1 | 1 |
| Protektor G3108 | 1 | 1 | 1 | 1 |
| Step 2 | | | | |
| Batch from step 1 | | | | |
| Step 3 | | | | |
| Batch from step 2 | | | | |
| Rhenogran TBBS-80 | 1.2 | 1.2 | 1.2 | 1.2 |
| Sulfur | 1.5 | 1.5 | 1.5 | 1.5 |

The natural rubber is an SMR 10 (from Malaysia, ML(1+4) 100° C.=60-70).

Vulkanox HS/LG is a TMQ from Rhein-Chemie GmbH Mannheim. Rhenogran TBBS-80 is an 80% N-tert.-butyl-2-benzothiazole sulfenamide accelerator from Rhein-Chemie GmbH Mannheim.

The rubber compounds are produced in an internal mixer according to the mixing instructions in Table 14.

TABLE 14

| Step 1 | |
|---|---|
| Settings | |
| Mixer | Brabender 350 S |
| Speed | 70 min$^{-1}$ |
| Ram force | 5.5 bar |
| Empty volume | 0.39 l |
| Fill ratio | 0.68 |
| Flow temp. | 90° C. |
| Mixing process | |
| 0 to 1 min | Natural rubber |
| 1 to 2 min | ½ carbon black, stearic acid, ZnO |
| 2 to 3 min | ½ carbon black, Vulkanox 4020, Vulkanox HS/LG, Protector G3108 |
| 3 min | Clean and vent |
| 3 to 5 min | Mix and remove (change speed if necessary) |
| Batch temp. | 145-155° C. |
| Storage | 24 h at room temperature |

TABLE 14-continued

| Step 2 | |
|---|---|
| Settings | |
| Mixer | As for step 1 apart from: |
| Speed | 100 min$^{-1}$ |
| Flow temp. | 100° C. |
| Fill ratio | 0.66 |
| Mixing process | |
| 0 to 2 min | Break up batch from step 1 |
| 2 min | Remove |
| Batch temp. | 145-155° C. |
| Storage | 24 h at room temperature |
| Step 3 | |
| Settings | |
| Mixer | Troster roll WNU1 |
| Speed front | 20 min$^{-1}$ |
| Speed rear | 24 min$^{-1}$ |
| Roll temp. front | 40° C. |
| Roll temp. rear | 50° C. |
| Mixing process | |
| 0 to 2 min | Batch from step 2, sheet out |
| 2 to 4 min | Incorporate accelerator, sulfur |
| 4 to 6 min | Score 3x on left, 3x on right and pass through 8x with narrow nip and 3x with wide nip Remove sheet. |
| Batch temp. | <110° C. |

The results of the rubber test are summarized in Table 15.

TABLE 15

| Results Feature | Unit | Comparative blend 12 | Blend 13 | Blend 14 | Blend 15 |
|---|---|---|---|---|---|
| Vulcanization time | [min] | 25 | 25 | 25 | 25 |
| Dmin | [dNm] | 1.3 | 1.3 | 1.2 | 1.3 |
| Dmax − Dmin Specimen 1 | [dNm] | 17.0 | 18.5 | 18.6 | 18.1 |
| Tensile strength | [MPa] | 25.9 | 27.5 | 24.7 | 24.3 |
| Modulus 50% | [Mpa] | 1.4 | 1.6 | 1.5 | 1.5 |
| Modulus 100% | [MPa] | 2.5 | 3.0 | 2.7 | 2.7 |
| Modulus 200% | [Mpa] | 7.3 | 7.6 | 6.7 | 6.7 |
| Modulus 300% | [MPa] | 14.0 | 13.8 | 12.3 | 12.1 |
| Elongation at break MTS | [%] | 490 | 535 | 515 | 515 |
| E*, 60° C. | [MPa] | 8.0 | 8.4 | 8.5 | 8.2 |
| Loss factor tanδ 60° C. | [—] | 0.144 | 0.126 | 0.124 | 0.125 |

The rubber compounds according to the invention display a markedly higher Dmax-Dmin value, dynamic modulus (E* 60° C.) and modulus at low elongations in comparison to the reference blend. The tan δ 60° C. is reduced (lower rolling resistance) in comparison to the reference blend.

Further variations and modifications of the foregoing will be apparent to those skilled in the art and are intended to be encompassed by the claims appended hereto.

German priority applications 103 36 575.3 of Aug. 8, 2003, is relied on and incorporated herein by reference.

We claim:

1. A carbon black having attached thereto at least one organic group selected from the group consisting of an N-(4-thiocyanate alkyl)succinimide, N-(4-thiocyanate aryl) succinimide, N-(4-thiocyanate alkyl)amide and N-(4-thiocyanate aryl)amide group.

2. The carbon blank having at least one organic group according to claim 1, characterized in that the organic group an N-(4-thiocyanatophenyl) succinimide or N-(4-thiocyanatophenyl)amide.

3. A process for the production of a carbon black according to claim 1, comprising reacting carbon black with an organic compound containing an organic group which is a member selected from the group consisting of an N-(4-thiocyanate alkyl)succinimide, N-(4-thiocyanate aryl)succinimide, N-(4-thiocyanate alkyl)amide and N-(4-thiocyanate aryl)amide group.

4. The process for the production of a carbon black according to claim 1, comprising reacting a carbon black with a diazonium salt, wherein the diazonium salt contains a thiocyanate group.

5. A vulcanizable rubber compound, comprising at least one rubber or a blend of rubbers and a carbon black having organic groups according to claim 1.

6. The vulcanizable rubber compound according to claim 5, wherein the carbon black having organic groups is used in a quantity of 10 to 150 parts by weight, the parts by weight relating to 100 parts by weight of rubber.

7. Process for the production of a vulcanizable rubber compound according to claim 5, wherein the rubber or the blend of rubbers and the carbon black with organic groups are mixed in a mixer.

8. A moulded article obtained from a rubber compound according to claim 5 by vulcanization.

9. A rubber compound according to claim 5, characterized in that its dynamic rigidity and loss factor tan δ at 60° C. are improved in comparison to a rubber compound containing unmodified starting carbon black.

10. A vulcanized rubber compound, comprising at least one rubber or a blend of rubbers and a carbon black having organic groups according to claim 1.

11. The vulcanized rubber compound according to claim 10, wherein the carbon black having organic groups is used in a quantity of 10 to 150 parts by weight, the parts by weight relating to 100 parts by weight of rubber.

12. Process for the production of a vulcanized rubber compound according to claim 10, wherein the rubber or the blend of rubbers and the carbon black with organic groups are mixed in a mixer.

13. A rubber compound according to claim 10 in the forms of a pneumatic tire, tire tread, cable sheath, tube, drive belt, conveyor belt, roll covering, tire, shoe sole, sealing ring, profile or damping element.

* * * * *